United States Patent [19]

Post et al.

[11] Patent Number: 4,599,481

[45] Date of Patent: Jul. 8, 1986

[54] PROCESS FOR THE PREPARATION OF HYDROCARBONS

[75] Inventors: Martin F. M. Post; Swan T. Sie, both of Amsterdam, Netherlands

[73] Assignee: Shell Oil Company, Houston, Tex.

[21] Appl. No.: 761,117

[22] Filed: Jul. 31, 1985

[30] Foreign Application Priority Data

Sep. 13, 1984 [NL] Netherlands ............ 8402807

[51] Int. Cl.$^4$ .................................................. C07C 2/00
[52] U.S. Cl. ............................................. 585/700
[58] Field of Search ............................................. 585/700

*Primary Examiner*—Paul R. Michl
*Assistant Examiner*—Alex H. Walker
*Attorney, Agent, or Firm*—Ronald R. Reper

[57] ABSTRACT

A process is disclosed for the preparation of $C_5$ and higher boiling hydrocarbons by contacting a mixture of carbon monoxide and hydrogen over a supported cobalt catalyst in which the cobalt is distributed in a specified inhomogeneous manner on the support.

16 Claims, No Drawings

PROCESS FOR THE PREPARATION OF HYDROCARBONS

BACKGROUND OF THE INVENTION

The invention relates to a process for the preparation of hydrocarbons by catalytic reaction of carbon monoxide with hydrogen.

The preparation of hydrocarbons from a $H_2/CO$ mixture by contacting this mixture at elevated temperature and pressure with a catalyst is known in the literature as the Fischer-Tropsch hydrocarbon synthesis. Catalysts suitable for the purpose are those comprising cobalt supported on a carrier. Such catalysts can be prepared by keeping particles of a porous carrier in contact with a solution of a cobalt compound for a considerable period of time, then removing the solvent and calcining and activating the composition obtained. Thus are generally obtained catalyst particles in which the cobalt is homogeneously distributed over the carrier material, viz. at every point of the catalyst particle the cobalt concentration present is virtually the same.

An investigation into the use of catalysts comprising cobalt on a carrier for preparing hydrocarbons from $H_2/CO$ mixtures has found that the $C_5+$ selectivity (selectivity to obtain $C_5$ and higher boiling hydrocarbons in the product) of these catalysts is highly dependent on the way in which the cobalt is distributed over the carrier material. It has been found that catalysts in which the cobalt is inhomogeneously distributed over the carrier material show a much higher $C_5+$ selectivity than similar catalysts where the cobalt is distributed homogeneously over the carrier, provided that said inhomogeneous distribution meets certain requirements. In order to assess the inhomogeneity of the cobalt distribution over the catalyst particles, the latter are taken to be composed of a kernel surrounded by a peel, the kernel being of such a shape that at every point of the kernel perimeter the shortest distance (d) to the perimeter of the peel is the same and that d is equal for all catalyst particles under consideration and has been chosen such that the quantity of cobalt present in the total peel volume ($\Sigma V_p$) is 90% of the quantity of cobalt present in the total volume of the catalyst particles under consideration ($\Sigma V_c$). It has been found that the catalysts having an inhomogeneous cobalt distribution show no significantly improved $C_5+$ selectivity as related to catalysts with homogeneous cobalt distribution, unless the inhomogeneous cobalt distribution is such as to meet the requirement $$(\Sigma V_p/\Sigma V_c) < 0.85$$

For determining $\Sigma V_p$ the "electron microprobe analysis" method can very suitably be used. The electron microprobe analysis procedure is described in Instrumental Methods Analysis D. Van Nostrand Co., New York, (1974) 5th Ed. H. H. Willard et al, Ed. page 272.

SUMMARY OF THE INVENTION

The present patent application therefore relates to a process for the preparation of hydrocarbons by catalytic reaction of carbon monoxide with hydrogen, in which a mixture of carbon monoxide and hydrogen is contacted at elevated temperature and pressure with a catalyst comprising cobalt supported on a carrier, and in which the cobalt is distributed over the carrier in such a manner as to satisfy the relation $$(\Sigma V_p/\Sigma V_c) < 0.85,$$

wherein $\Sigma V_p$ and $\Sigma V_c$ having the meanings given hereinabove.

DESCRIPTION OF PREFERRED EMBODIMENTS

Catalysts having a suitable inhomogeneous cobalt distribution can be prepared in a simple manner by keeping particles of a porous carrier immersed in water for about 30 minutes and, upon dripdrying, keeping the water-saturated carrier several times—each time for about 30 seconds—immersed in a solution of a cobalt salt in water, with the cobalt-loaded carrier being dried and calcined after each immersion. Organic and inorganic salts of cobalt dissolved in suitable solvents such as alcohols, hydrocarbons, ethers, esters and the like may also be suitably employed to impregnate the support, as will be apparent to those skilled in the art.

The catalysts used in the process according to the invention contain cobalt supported on a carrier. Very suitable carriers are, inter alia, silica, alumina and silica-alumina. Preference is given to the use of silica as carrier. The quantities of cobalt present on the catalysts may vary between wide ranges. Preferably use is made of catalysts which contain 3–60 parts by weight of cobalt per 100 parts by weight of carrier material. The catalysts used in the process according to the invention preferably include one or more promoters. Suitable promoters for the present cobalt catalysts are iron, magnesium, zinc and thorium. Preferably use is made of catalysts containing zirconium, titanium, chromium or ruthenium as promoter. Special preference is given to the use of zirconium as promoter. The preferred quantities of promoter present in the cobalt catalysts are dependent on the way in which it has been deposited. In the case of catalysts in the preparation of which the cobalt was deposited on the carrier first, and the promoter next, preference is given to catalysts comprising 0.1–5 parts by weight of the promoter per 100 parts by weight of carrier. In the case of catalysts in the preparation of which the promoter was deposited on the carrier first, and the cobalt next, preference is given to catalysts comprising 5–40 parts by weight of the promoter per 100 parts by weight of carrier.

In the process according to the invention it is essential that a catalyst be used in which the cobalt is inhomogeneously distributed over the carrier in the correct manner. If, in addition to cobalt, the catalyst comprises a promoter, such as zirconium, the latter may be distributed over the carrier either homogeneously or inhomogeneously. Homogeneous distribution of the promoter will occur when the promoter is deposited on the carrier by way of conventional impregnation, either proceeding or following the deposition of the cobalt on the carrier. Inhomogeneous distribution of the promoter may occur when the cobalt and the promoter are deposited simultaneously by co-impregnation, special measures having been taken to bring about the desired inhomogeneous distribution of cobalt over the carrier.

Before becoming eligible for use in the preparation of hydrocarbons from a $H_2/CO$ mixture, the cobalt catalysts should be activated. This activation can suitably be carried out by contacting the catalysts at a temperature between 200° and 350° C. with hydrogen or a hydrogen-containing gas.

The conversion of the $H_2/CO$ mixture into hydrocarbons according to the invention is preferably carried out at a temperature of 125°–350° C. and particularly 175°–275° C. and a pressure of 5–100 bar and particularly of 10–75 bar. Further, the conversion is preferably carried out by contacting the $H_2/CO$ mixture with a catalyst which is present in the form of a fixed bed having an external surface area ($S_E$) between 5 and 70 cm$^2$/ml. External surface area is determined by the procedure in Direct Characterization of Fine Particles, J. Wiley and Sons, New York, (1981) B. H. Kayes Ed., page 325. In this case it is particularly preferred to use a catalyst for which $$0.03 \times \sqrt{S_E} < \frac{\Sigma V_p}{\Sigma V_c} < 0.3 \times \sqrt{S_E}$$

$H_2/CO$ mixtures which are eligible to be converted into hydrocarbons according to the invention can very suitably be obtained by steam reforming or partial oxidation starting from light hydrocarbons, such as natural gas.

The $H_2/CO$ mixture which is converted into hydrocarbons according to the invention preferably has a $H_2/CO$ molar ratio lower than 1.5, it is preferred to increase the latter to a value lying between 1.5 and 2.5 and in particular between 1.75 and 2.25, before the feed is contacted with the cobalt catalyst. The $H_2/CO$ molar ratio of hydrogen-poor $H_2/CO$ mixtures can be increased by, inter alia, addition of hydrogen, removal of carbon monoxide, mixing with a hydrogen-rich $H_2/CO$ mixture or by subjecting the hydrogen-poor $H_2/CO$ mixture to the CO-shift reaction.

The process according to the invention can suitably be used as an independent process in which unconverted synthesis gas can be recirculated, if desired. Further, the process according to the invention can very suitably be used as the first step in a two-step process for the preparation of middle distillates from $H_2/CO$ mixtures. For it has been found that catalysts containing silica, alumina or silica-alumina as carrier and cobalt together with zirconium, titanium, chromium and/or ruthenium as catalytically active metals, which catalysts have been prepared by depositing the metals concerned on the carrier material by impregnation, yield a product substantially consisting of unbranched paraffins whose high-boiling part can be converted in high yield into middle distillates by subjecting it to a hydrocracking treatment.

Although in the preparation of middle distillates from the product obtained over the cobalt catalyst the part of the product whose initial boiling point lies above the final boiling point of the heaviest middle distillate desired as end product will do as feed for the hydrocracking, the total $C_5+$ fraction of the product prepared over the cobalt catalyst may also be used for the purpose, if desired.

The hydrocracking is carried out by contacting the fraction to be treated at elevated temperature and pressure and in the presence of hydrogen with a catalyst containing one or more Group VIII noble metals on a carrier. The hydrocracking catalyst used by preference is a catalyst comprising 0.2–1% w of platinum or palladium supported on silica-alumina as carrier. The hydrocracking treatment is preferably carried out at a temperature of 250°–350° C. and a pressure of 10–75 bar.

The invention is now illustrated with the aid of the following example.

EXAMPLE

Catalyst Preparation

Three $Co/Zr/SiO_2$ catalysts (catalysts 1–3) were prepared as follows, starting from a spherical silica carrier dried at 120° C.

Catalyst 1

The silica carrier was contacted at a temperature of 20° C. for 15 minutes with a solution of cobalt nitrate in water. The quantity of solution used was such that its volume corresponded substantially with the pore volume of the carrier. The solution had a viscosity, measured at 60° C., of 1.7 cS. After drying and calcining at 500° C. the cobalt-loaded carrier was kept in contact with a solution of zirconium nitrate in water. In this case, too, the quantity of solution used corresponded substantially with the pore volume of the carrier. Finally the cobalt- and zirconium-loaded carrier was dried and calcined at 500° C.

Catalyst 2

The silica carrier was kept immersed in water of 20° C. for 30 minutes. After dripdrying the water-saturated carrier was immersed three times—each time for 30 seconds—at a temperature of 20° C. in the same solution of cobalt nitrate in water as was used in the preparation of catalyst 1. After each immersion the material was dried and calcined at 500° C. Subsequently, zirconium was deposited on the cobalt-loaded carrier in a way identical to that described for the preparation of catalyst 1.

Catalyst 3

This catalyst was prepared in substantially the same way as catalyst 2, he difference being that in the present case four immersions in the cobalt nitrate solution were performed.

Further information concerning catalysts 1–3 is given in the table.

Catalyst Testing

Catalysts 1–3 were used in three experiments (experiments 1–3) in the preparation of hydrocarbons from a mixture of carbon monoxide and hydrogen having a $H_2/CO$ molar ratio 2. The experiments were carried out at a pressure of 20 bar and a space velocity of 600 Nl.l$^{-1}$.h$^{-1}$ in a reactor containing a fixed catalyst bed having $S_E$ of 13 cm$^2$/ml. Preceding the testing the catalysts were activated by subjection to a hydrotreatment at 250° C. Further information on experiments 1–3 is given in the table.

Of the experiments mentioned in the table only experiments 2 and 3 are experiments according to the invention. These experiments, which were carried out using a catalyst for which $$(\Sigma V_p/\Sigma V_c) < 0.85,$$

led to relatively high $C_5+$ selectivities. Experiment 1 falls outside the scope of the invention and has been included in the patent application for comparison. The $C_5^+$ selectivity found in this experiment, which was carried out using a catalyst for which $$(\Sigma V_p / \Sigma V_c) < 0.85,$$

was considerably lower.

TABLE

| Experiment No. | 1 | 2 | 3 |
|---|---|---|---|
| Catalyst No. | 1 | 2 | 3 |
| Cobalt load, g Co/100 g $SiO_2$ | 22 | 18 | 22 |
| Zirconium load, g Zr/100 g $SiO_2$ | 0.9 | 0.9 | 0.9 |
| $\frac{\Sigma V_p}{\Sigma V_c}$ | 0.88 | 0.75 | 0.73 |
| Temperature of synthesis gas conversion, °C. | 230 | 235 | 225 |
| Nl synthesis gas converted per g Co per h | 5.1 | 7.4 | 5.8 |
| $C_5^+$ selectivity, % w | 59 | 65 | 66 |

We claim:

1. A process for the preparation of hydrocarbons by catalytic reaction of carbon monoxide with hydrogen, wherein a mixture of carbon monoxide and hydrogen is contacted at a temperature of 125°–350° C. and pressure of 5–100 bar with a catalyst comprising cobalt supported on a carrier, the cobalt being distributed over the carrier in such a way as to satisfy the relation $$(\Sigma V_p / \Sigma V_c) < 0.85,$$

wherein $\Sigma V_c$ represents the total volume of the catalyst particles under consideration and $\Sigma V_p$ is found by totalizing the peel volume present in the catalyst particles, when the latter is taken to be composed of a kernel surrounded by a peel, the kernel being of such a shape that at every point of the kernel perimeter the shortest distance (d) to the perimeter of the peel is the same, and that d is equal for all catalyst particles under consideration and has been chosen such that the quantity of cobalt present in $\Sigma V_p$ is 90% of the quantity of cobalt present in $\Sigma V_c$.

2. A process as in claim 1, wherein the catalyst carrier comprises silica, alumina or silica-alumina.

3. A process as in claim 1, wherein the catalyst comprises 3–60 parts by weight of cobalt per 100 parts by weight of carrier.

4. A process as in claim 1, wherein the catalyst comprises 5–50 parts by weight of cobalt per 100 parts by weight of carrier.

5. A process as in claim 1, wherein the catalyst comprises at least one promoter selected from zirconium, titanium, chromium and ruthenium.

6. A process as in claim 1, wherein the catalyst comprises 0.1–5 parts by weight of promoter per 100 parts by weight of carrier, and during the catalyst preparation the cobalt was deposited on the carrier first and the promoter next.

7. A process as in claim 1, wherein the catalyst comprises 5–40 parts by weight of promoter per 100 parts by weight of carrier and during the catalyst preparation the promoter was deposited on the carrier first and the cobalt next.

8. A process as in claim 1, wherein the catalyst comprises silica as carrier and zirconium as promoter.

9. A process as in claim 1, carried out at a temperature of 175°–275° C. and a pressure of 10–75 bar.

10. A process as in claim 1, wherein the $H_2/CO$ mixture is contacted with a catalyst which is present in the form of a fixed bed having an external surface area ($S_E$) between 5 and 70 $cm^2$/ml.

11. A process as in claim 10, wherein a catalyst is used for which $$0.03 \times \sqrt{S_E} < \frac{\Sigma V_p}{\Sigma V_c} < 0.3 \times \sqrt{S_E}.$$

12. A process as in claim 1, wherein the $H_2/CO$ mixture has been obtained by steam reforming or by partial oxidation of natural gas.

13. A process as in claim 1, wherein the $H_2/CO$ mixture has an $H_2/CO$ molar ratio higher than 1.5.

14. A process as in claim 1, wherein the $H_2/CO$ mixture has a $H_2/CO$ molar ratio between 1.75 and 2.25.

15. A process as in claim 1, comprising the further steps of the first step in a two-step process for the preparation of middle distillates from $H_2/CO$ mixtures, that in the first step use is made of a catalyst which comprises silica, alumina or silica-alumina as carrier and cobalt together with zirconium, titanium, chromium and/or ruthenium as catalytically active metals, which catalyst has been prepared by depositing the metals concerned onto the carrier material by fractionating the product to obtain a fraction whose initial boiling point lies above the final boiling point of the heaviest middle distillate desired as end product and, hydrocracking said high boiling fraction by contacting it at a temperature of 250°–350° C. and a pressure of 10–75 bar with a catalyst comprising one or more noble metals from Group VIII supported on a carrier.

16. A process as in claim 1, wherein the hydrocracking catalyst comprises 0.2–1% w of a metal selected from platinum and palladium supported on silica-alumina as carrier.

* * * * *

Adverse Decisions In Interference

Patent No. 4,599,481, Martin F. M. Post, Swan T. Sie, PROCESS FOR THE PREPARATION OF HYDROCARBONS, Interference No. 102,202, final judgment adverse to the patentees rendered March 12, 1997, as to claims 1-16.

*(Official Gazette October 27, 1998)*